United States Patent [19]

Nash

[11] 4,168,280
[45] Sep. 18, 1979

[54] METHOD FOR SYNTHESIS OF 2-HYDROXY-3-METHYL CYCLOPENT-2-ENE-1-ONE

[75] Inventor: William D. Nash, Odessa, Tex.

[73] Assignee: El Paso Products Company, Odessa, Tex.

[21] Appl. No.: 907,730

[22] Filed: May 19, 1978

[51] Int. Cl.² .............................................. C07C 45/00
[52] U.S. Cl. ............................. 260/586 R; 260/586 C
[58] Field of Search .................................... 260/586 R

[56] References Cited

U.S. PATENT DOCUMENTS

| 2,228,268 | 1/1941 | Hansley | 260/586 R |
|---|---|---|---|
| 3,402,181 | 9/1968 | Erickson et al. | 260/586 R |
| 3,628,970 | 12/1971 | Stephens et al. | 260/586 R |
| 3,652,643 | 3/1972 | Leir | 260/586 R |
| 3,754,016 | 8/1973 | Oberhausli | 260/586 R |
| 3,907,896 | 9/1975 | Calame et al. | 260/586 R |
| 3,922,296 | 11/1975 | McFearin | 260/586 R |
| 3,969,408 | 7/1976 | Kyomosi et al. | 260/586 R |

OTHER PUBLICATIONS

House, "Modern Synthetic Reactions," 2nd Edition, pp. 169–171 (1972) W. A. Benjamin Inc., Menlo Park, Calif.

Primary Examiner—Norman Morgenstern

[57] ABSTRACT

The known compound 2-hydroxy-3-methyl cyclopent-2-ene-1-one, used as a flavor imparting agent and commonly called maple lactone, is synthesized by a modified acyloin condensation of esters of 2-methyl glutaric acid in which oxygen is introduced in a specific manner to the reaction system.

5 Claims, No Drawings

METHOD FOR SYNTHESIS OF 2-HYDROXY-3-METHYL CYCLOPENT-2-ENE-1-ONE

BACKGROUND OF THE INVENTION

1. Field of the Invention

The present invention relates to synthesis of flavoring agents, particularly maple lactone used as a modifier in such imitation flavorings as walnut, rum, caramel, butterscotch and coffee or directly in imitation maple syrup. The product of the invention results from a single reaction stage which is essentially an acyloin condensation of dimethyl-2-methyl glutarate (or other lower alkyl ester of 2-methyl glutaric acid) modified by introduction of oxygen, preferably air, to the reaction system thereby modifying the course of the reaction to yield the desired product.

2. Description of the Prior Art

It is generally recognized that the product obtained according to a preferred embodiment of the process of this invention is a material having a sweet characteristic flavor reminiscent of walnuts and which, heretofore has been employed as flavoring additive in a variety of food products, either as the primary flavor or as modifier of other flavoring agents. The compound is a white crystalline solid which has been found to be useful as the primary flavoring agent in imitation maple syrup, a use from which it derives the appellation "maple lactone".

The compound is tautomeric with the corresponding diketone, 3-methyl cyclopentane-1,2 dione.

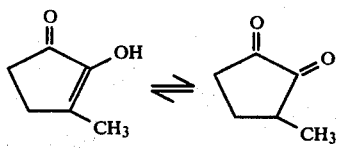

Much of the literature on the subject identifies the product by the name of the diketone tautomer.

Because of the general acceptance of this product, the art has been interested in attempts to develop economical and commercially practicable processes for synthesis of the same from available raw materials and intermediates. In general, the syntheses heretofore proposed have been multi-step processes, necessarily involving a yield of less than the theoretical value at each step, the losses being cumulative such that ultimate yield of maple lactone is reduced to a substantial degree.

One such prior process is described in U.S. Pat. No. 3,922,296, granted Nov. 25, 1975 to the assignee of the present application. (U.S. Classification 260/468K) According to that recent patent esters of glutaric and oxalic acids are condensed in the presence of an alkali metal alkoxide while dissolved in an aprotic solvent to form 3,5 dicarboalkoxy-cyclopentane-1,2 dione dialkali metal salts. The salts are alkylated to form 2-alkoxy-3,5 dicarboalkoxy-5-alkylcycyclopent-2-ene-1-one, which is then hydrolyzed to yield the desired product. That commonly assigned patent provides extensive review of prior art which is hereby incorporated by reference.

Additional discussions of prior practices in synthesis of carbonyl derivatives of five member carbon rings are found in U.S. Pat. Nos. 2,865,962, 3,349,130, 3,518,296, 3,652,643 and 3,671,589.

As stated above, the classical acyloin condensation has been modified to accomplish the purposes of the invention. That classical reaction involves bimolecular condensation and reduction of aliphatic esters by the action of metallic sodium in a solvent such as liquid ammonia of xylene and usually with a cosolvent such as diethyl ether. Generally the methyl or ethyl esters are employed. The reaction is discussed in detail by S. M. McElvain, Organic Reactions, 4, 256 (Wiley, 1948) and by K. T. Finley, Chemical Reviews, 64, 573 (1964). Both of these authors describe synthesis of cyclic compounds having upwards of seven carbon atoms by intramolecular condensation of esters of dicarboxylic acids, Finley also noting "the only successful application of the heterogeneous acyloin reaction to the preparation of small rings" is condensation of a phthalate ester to bicyclo octane having a four member ring. Formation of the five member cyclic acyloin 4,4-dimethylcyclopentan-2-ol-1-one from dimethyl beta, beta dimethyl glutarate is reported by Rouse and Tyler, Journal of Organic Chemistry, 26, 3525 (1961).

The acyloin condensation requires that the reaction mixture be free of oxygen. Very small amounts of oxidizing agent cause substantial decrease in the amount of acyloin product obtained. Instead, by-products are formed including such materials as bi-molecular acyloins, polymer and polymeric acid, diols, dioldiones and alpha-diketones.

In discussing cyclization by the acyloin condensation, McElvain (pp 262, 263) emphasizes the importance of excluding oxygen. He cites disastrous drops in yield when the nitrogen used for inert atmosphere contained as little as 4% oxygen. He notes that the cyclic acyloins in the presence of sodium alkoxides (which are formed during the course of the reaction) are extremely sensitive to oxygen. The small amount of oxygen present in commercial nitrogen is sufficient to transform an intermediate into the cycle diketone and other secondary reaction products.

SUMMARY OF THE INVENTION

It has now been found that the acyloin reaction is cyclizing by intramolecular condensation of dicarboxylic acid esters having chain of five carbon atoms (i.e. the carboxyl carbons are joined through a chain of three intermediate carbon atoms) may be diverted to yield, as a primary product, cyclic compounds of five carbon atoms in the ring and having two adjacent keto groups (or tautomeric forms). This is accomplished by introduction of minor amounts of oxygen to the reaction. Preferably, the oxygen introduction is controlled as to time and amount for production of maximum quantities of the unsaturated keto alcohol, or of the tautomeric cyclic diketone.

The course of the reaction is typified by condensation of 2-methyl glutarate esters, such as the methyl and ethyl esters according to the equation:

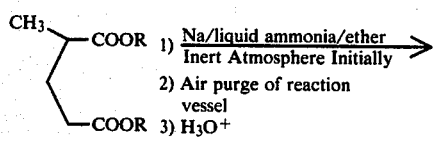

R is methyl or ethyl

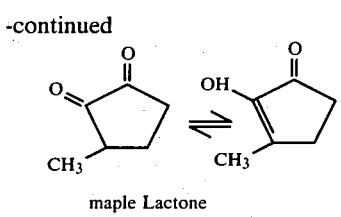

maple Lactone

By this technique yields of crude maple lactone equivalent to 57% of theoretical based on starting ester have been achieved.

In all respects other than controlled addition of oxygen, the present process conforms to the conditions normally set for the acyloin condensation. The reaction is induced by metallic sodium, potassium or other alkali metal, e.g. sodium-potassium alloy. The reaction is conducted in a solvent preferably liquid ammonia, ether, benzene, xylene or mixtures such as ammonia plus diethyl ether. The reaction is conducted at temperatures ranging upwardly from 0° C. to reflux temperature of the solvent with adequate stirring to promote contact of reactant ester with the alkali metal.

The reaction is initiated under an inert atmosphere as is normal in the acyloin condensation. Oxygen-free nitrogen is used to purge the reaction vessel before the reaction is initiated and circulation of such nitrogen (or other suitable oxygen free gas) continues as the reaction proceeds. A convenient way to apply the invention is to purge the reaction vessel of solvent by introduction of air as the reaction abates, evidenced by sodium disappearance or color changes.

The novel synthesis here described is a general method for producing compounds analagous to maple lactone from dimethyl, diethyl and ethyl, methyl esters of glutaric acid substituted by at least one methyl or ethyl group at the 2- or 3- position or both. The shift to these desirable products is induced by introduction of oxygen, preferably air, to the system after addition of reactants is complete. In a preferred embodiment, air is employed to purge the solvent from the reaction zone. Except for that variation, generally regarded in the art as undesirable, the synthesis is conducted in accordance with known, classical procedures.

SPECIFIC EMBODIMENTS OF THE INVENTION

Typical experimental runs demonstrate that the invention provides a technique for modifying the classical acyloin condensation to produce unsaturated homologues of acyloins, tautomeric with diketones, as primary products.

EXAMPLE 1

Maple lactone was produced from 2-methyl dimethyl glutarate (prepared by the method described at JACS, 42, 313) in a dry system free of oxygen under flow of dry nitrogen. A charge of 8.84 grams of the ester in anhydrous diethyl ether was added in titration fashion to 5 grams of metallic sodium in 125 ml. of liquid ammonium over a period of about 2 hours while agitating with a magnetic stirrer. When the solution turned yellow, more sodium was added until the solution remained blue after all the ester had been added. More ether, about 125 ml., was added and the nitrogen flow was replaced by air overnight, purging the system of solvents.

Ether in an amount of about 150 ml. was added to the resultant dry residue and 30 ml. of 5% hydrochloric acid was dripped in slowly. The solution became viscous and sticky to such extent that the magnetic stirrer was inoperative. With the aid of 100 ml. of ethyl acetate, the mass was loosened to yield a dark reddish liquid phase and a clear organic phase.

The crude product was transferred from the reaction pot to a separatory funnel. Clear separation of layers was achieved upon addition of about 20 ml. of concentrated hydrochloric acid solution.

The layers were separated and the ethyl acetate/ether layer was washed with 30 ml. of water and concentrated by evaporation. The aqueous phase plus 30 ml. from water wash of the organic phase was saturated with ammonium chloride and extracted with 100 ml. of chloroform. The extract phase was washed with 30 ml. of water and added to the concentrate from evaporation of the washed organic layer. Acid seemed detectable by odor, therefore the solution was washed with 30 ml. of brine and concentrated by evaporation to yield 4.5 grams of yellow crystals as crude product which was dissolved in ethyl acetate and hexane and left to evaporate open to ambient air, resulting in crystalization.

The product was found to be about 30 weight percent yield of theoretical as 2-hydroxy-3-methyl cyclopent-2-ene-1-one.

EXAMPLE 2

Following the procedure described at JACS 75, 3998, a condensation was conducted of 4.1 grams 2-methyl diethyl glutarate in the presence of 2 grams of sodium. After addition of 200 ml. of ether, the reaction mixture was maintained under nitrogen overnight and air was introduced in the presence of a catalytic amount of cupric acetate to purge the solvent. To the yellow cake in the reaction vessel were added 200 ml. of ether with stirring and the solution was evaporated, followed by addition of 150 ml. of 3 N hydrochloric acid and 250 ml. of ether. Layers were separated and aqueous layer saturated with sodium chloride, then extracted with two portions of 150 ml. each of ether. The extracts were combined, filtered through sodium sulfate and evaporated to yield 3 grams of product. Based on vapor phase chromatography, yield of maple lactone was estimated at 26% of theoretical.

EXAMPLE 3

The reaction was conducted in a 3-neck, one liter flask equipped with a magnetic stirrer, a reflux condenser cooled by dry ice, a dropping funnel for introduction of reactants and a source of nitrogen to maintain the system under dry, oxygen-free nitrogen. All glassware was carefully dried before addition of solvent and reactants. To about 0.8 liter of liquid ammonia in the flask, 12.0 grams of sodium were added. A solution of 23.283 grams of 2-methyl, diethyl glutarate in 230 ml. of anhydrous diethyl ether was added over a period of 2.5 hours, noting that the solution produced an immediate precipitate which caused difficulty at the addition funnel. The bulk of the ammonia was swept out of the pot with nitrogen over a period of 1.5 hours to leave a thick residue cake to which 350 ml. of dry ether was added and the vessel purged with air overnight.

To the residue, 200 ml. of ether and 500 ml. of 3 N hydrochloric acid were added over a five minute interval. The resultant layers were separated and the aqueous phase extracted twice with 500 ml. of ether at each extraction. The combined ether extracts were concentrated to 600 ml. and dried over sodium sulfate. Ether removal by rotary evaporation at reduced pressure and vacuum pumping gave 12.5 grams of a dark oil. An additional 5 grams of dark reddish oil was obtained by further ether extraction over a period of 7 hours. Analysis showed a yield of 2.0 grams maple lactone.

EXAMPLE 4

A run similar to that of Example 3 employed 16.540 grams of ester dissolved in 240 ml. of ether, which was added to 9.0 grams of sodium in about 1000 ml. of anhydrous liquid ammonia. An additional 2.5 grams of sodium were added when the reacting solution turned yellow prior to addition of the last 150 ml. of ester/ether solution. Addition of the solution of ester was completed over a period of 4 hours. The solution was then stripped by air purge overnight to remove ammonia. The solution was placed under nitrogen atmosphere and 150 ml. of 3 N hydrochloric acid added cautiously during a ten minute interval, followed by 300 ml. of ether. Ether extraction of the aqueous phase with two 300 ml. portions, concentration, adddition of hexane and boiling yielded 32% of theoretical as maple lactone.

EXAMPLE 5

Following a procedure like that of Example 3, the dimethyl ester was reacted to produce 41% of theoretical yield of maple lactone. To 9 grams of sodium in 1000 ml. of liquid ammonia a solution of 15.383 grams of ester in 240 ml. of ether was added dropwise over a period of 3 hours, 25 minutes. A dark blue solution resulted which was stirred 30 minutes longer without color change of significance, whereupon additional ester solution (1.187 grams ester in 40 ml. ether) was introduced and the solution turned yellow. Total ester introduced amounted to 16.57 grams.

The line for introduction of nitrogen was then changed to air supply. After bulk of the ammonia was evaporated, 200 ml. of ether was added. Ether was evaporated and the reaction product was placed on a 55° C. water bath after addition of 100 ml. more ether. After evaporation, 125 ml. of ether was added and addition of 160 ml. of 3 N hydrochloric acid was begun. The solution turned very dark, whereupon 300 ml. of ether was added during course of the acidification (15 minutes). The separated aqueous layer was extracted with ether, dried and examined to find total yield equal to 41% of theoretical.

EXAMPLE 6

A yield of 43% maple lactone was obtained by addition of 48.49 grams of 2-methyl dimethyl glutarate (98.6% purity), as solution in 500 ml. of ether, to 29 grams of sodium in 1500 ml. of liquid ammonia. The reaction was conducted in a 3 liter 3-neck flask, pre-dried and maintained under nitrogen. The ester was added over a period of 3.5 hour resulting in a solution which turned yellow almost immediately on completion of addition of ester.

Ammonia was swept from the vessel by dry air overnight, leaving a dark residue which was crusty and rather easily fragmented. The magnetic stirrer was replaced by a motor driven stirrer and 500 ml. of solvent ether added cautiously. A 55° C. water bath was placed under the flask and air employed to sweep away the bulk of the ether, leaving a powder of large granules. To the powder, 700 ml. of solvent ether were added, the system placed under nitrogen atmosphere and 400 ml. of 3 N hydrochloric acid dropped in. Noting that metallic sodium was still present on the walls of the vessel, this addition was conducted with caution. That problem can probably be avoided by first introducing methyl alcohol or the like.

Acidification consumed about 70 minutes, resulting in separation of two clear phases, 450 ml. aqueous and 500 ml. ether solution. The aqueous phase was extracted with ether and worked up to a total yield of 43% maple lactone.

EXAMPLE 7

A further run was conducted by similar technique in addition of 52.8270 grams of 2-methyl dimethyl glutarate (97.87% purity) in 500 ml. of ether to 31.5 grams of sodium in 1400 ml. of liquid ammonia. After sweeping the vessel with dry air overnight, acidification and ether extraction of aqueous phase, light yellow crystals of maple lactone were isolated in an amount equal to 33% of theoretical yield.

I claim:

1. In a process for acyloin condensation of an ester having the formula:

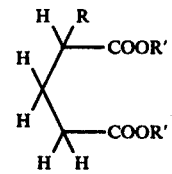

where R represents hydrogen, methyl or ethyl and R' represents methyl or ethyl, by adding the ester to an alkali metal in an acyloin condensation solvent; the improvement resulting in substantial yield as product of 2-hydroxy cyclopent-2-ene-1-one having substituents R corresponding to substituents R of said ester which comprises introducing oxygen to the mixture resulting from said addition.

2. The process of claim 1 wherein said ester is 2-methyl dimethyl glutarate and said product is 2-hydroxy-3-methyl cyclopent-2-ene-1-one.

3. The process of claim 1 wherein said ester is 2-methyl diethyl glutarate and said product is 2-hydroxy-3-methyl cyclopent-2-ene-1-one.

4. The process of claim 1 wherein said alkali metal is sodium and said solvent is liquid ammonia.

5. The process of claim 1 wherein air is introduced to said mixture, thereby purging said solvent.

* * * * *